(12) United States Patent
Tanaka (10) Patent No.: US 7,148,244 B2
(45) Date of Patent: Dec. 12, 2006

(54) MEDICINES IN CONTROLLING VPR FUNCTION

(75) Inventor: Hideki Tanaka, Kyoto (JP)

(73) Assignee: Nippon Shinyaku Co. Ltd., Kyoto (JP)

( * ) Notice: Subject to any disclaimer, the term of this patent is extended or adjusted under 35 U.S.C. 154(b) by 30 days.

(21) Appl. No.: 10/474,600

(22) PCT Filed: Apr. 25, 2002

(86) PCT No.: PCT/JP02/04125

§ 371 (c)(1),
(2), (4) Date: Oct. 9, 2003

(87) PCT Pub. No.: WO02/087577

PCT Pub. Date: Nov. 7, 2002

(65) Prior Publication Data

US 2004/0209927 A1     Oct. 21, 2004

(30) Foreign Application Priority Data

Apr. 26, 2001 (JP) .............................. 2001-129912

(51) Int. Cl.
*A61K 31/44* (2006.01)
*C07D 211/72* (2006.01)
(52) U.S. Cl. ....................... 514/345; 514/351; 546/290; 546/329
(58) Field of Classification Search ................... 546/40, 546/34; 514/345, 351
See application file for complete search history.

(56) References Cited

FOREIGN PATENT DOCUMENTS

| EP | 754682 A1 | 1/1997 |
| JP | 2001 261649 A | 9/2001 |
| WO | WO 95/31901 | 11/1995 |
| WO | WO 96/19437 | 6/1996 |
| WO | WO 01/21598 A1 | 3/2001 |

OTHER PUBLICATIONS

Human Immunodeficiency Virus Type 1 Vpr Induces Apoptsis Through Caspase Activation Journal of Virology, Apr. 2002, vol. 74, No. 7, pp. 3105-3111.
C.K. Arunagiri, et al., A C-Terminal Domain of HIV-1 Accessory Protein Vpr is Involved in Penetration, Mitochondrial Dysfunction and Apoptosis of Human CD4+ Lymphocytes, Apoptosis 2, 69-76 (1997).
I.G. Macreadie, et al., A Domain of Human Immunodeficiency Virus Type 1 Vpr Containing Repeated H(S/F)RIG Amino Acid Motifs Causes Cell Growth Arrest and Structural Defects, Proc. Natl. Acad. Sci. USA 92, 2770-2774 (1995).
S.C. Piller, et al., Extracellular HIV-1 Virus Protein R Causes a Large Inward Current and Cell Death in Cultured Hippocampal Neurons: Implications for AIDS Pathology, Proc. Natl. Acad. Sci. USA 95, 4595-4660 (1998).
Derwent publication-abstract of JP2001 261649A.
Nishizawa, et. al. "Induction of Apoptosis by the Vpr Protein of Human Immunodeficiency Virus Type 1 Occurs Independently of G2 Arrest of the Cell Cycle"; Virology, 276, 16-26 (2000).

*Primary Examiner*—Kamal A. Saeed
*Assistant Examiner*—Robert Shiao
(74) *Attorney, Agent, or Firm*—Greenberg Traurig LLP (57) ABSTRACT

A Vpr function regulating composition useful in the treatment of subjects infected with HIV or having AIDS, wherein the composition comprises an aminostilbazole derivative represented by the following formula [1] or a salt thereof as an active ingredient:

A-B-D-E     [1]

wherein A represents heteroaryl or an oxide thereof, B represents ethenylene, D represents phenylene, and E represents the formula: —N(R)—SO$_2$-G wherein G represents phenyl, R represents hydrogen, alkyl, or —COR$^0$ (R$^0$ represents alkyl, alkoxy, aryloxy, 5- to 6-membered heteroaryl, heteroarylmethyl, aminoalkylene, or cyclic amino alkylene) or the like.

10 Claims, 3 Drawing Sheets

MEDICINES IN CONTROLLING VPR FUNCTION

TECHNICAL FIELD

The present invention relates to a Vpr function regulating agent and an anti-HIV agent.

BACKGROUND ART

In recent years, the prevalence of acquired immunodeficiency syndrome (AIDS) has been rapidly increased, and there is worldwide need for establishing methods for its prophylaxis and treatment. AIDS is caused by human immunodeficiency virus (HIV), a Lentivirus in the family Retroviridae. For HIV, at present, there are known two types of viruses, HIV-1 and HIV-2. HIV mainly infects CD4(+) T-lymphocytes in humans, anthropoid apes (chimpanzees), and others, and destroys them and causes AIDS.

As agents against AIDS are currently used inhibitors of reverse transcriptase characteristic of HIV [for example, zidovudine (AZT, ZDV), didanosine (ddI), zalcitabine (ddC)] and of viral proteolytic enzymes (for example, saquinavir) Actually, two types of agents having different mechanisms of action are combined. Although these are intended to kill HIV-1, they display side effects and may lead to the generation of viruses that are resistant to them by taking them over a long period of time, for example, and thus it cannot always be said that these agents are satisfactory ones.

The genome of a retrovirus has a major characteristic in that the genome is integrated into a chromosome of an infected cell through the phenomenon of reverse transcription. Accordingly, it is impossible for agents and others to eradicate the virus throughout the body, and thus infected individuals necessitate co-existence with the virus in their life.

Another characteristic of retroviruses is that they possess genes encoding for a group of proteins referred to as accessory proteins (for example, Nef, Vif, Vpr, Tat, Rev), in addition to genes for proteins constituting a virus (for example, Gag, Pol, Env). Among them, Vpr is a small protein consisting of 96 amino acids and has a variety of functions of, for example, transporting to the nucleus a viral genome-protein complex, designated as pre-integration complex (immature virus); arresting the cell cycle of infected cells at the G2/M period, thereby enhancing the efficiency of transcription of the virus genome within non-dividing cells such as macrophages; destroying surrounding cells (bystander cells) in lymph nodes via cell-membrane impairing activities. In fact, it is known that HIV-1 genome is actively replicated when an infected cell is at the G2/M period, and that an HIV-1 mutant deficient in Vpr results in extremely reduced production of mature viruses in macrophages.

It is also reported that Vpr suppresses the proliferation of infected cells, thereby promoting the destruction of infected T-cells, as well as inhibiting the establishment of HIV-1 persistent infection (Rogel M E et al., J. Vilol., 69: 882–888, 1995). This activity of Vpr suggests a possibility that Vpr is involved during the transition of the silent period to AIDS.

Vpr has homology in structure as well as in function homologous between simian immunodeficiency virus (SIV) and HIV-1 and HIV-2. Actually, it is shown that in monkeys, Vpr is essential for the onset of AIDS caused by SIV (Hoch J. et al., J. Virol., 69: 4807–4813, 1995).

As described above, Vpr is believed to be involved in the progression of each pathological stage by exerting its various functions at a particular period in the pathological stages from the initial infection to the onset of AIDS. Therefore, compounds that regulate Vpr functions display activities of, for example, 1) inhibiting HIV-1 infection of macrophages and others, which will become reservoirs of HIV in lymphoid tissues such as thymus, and production of mature viruses; 2) inhibiting apoptosis of HIV-infected CD4(+) T-cells, thereby causing the host immune system to induce cytotoxic lymphocytes (CTLs) against infected cells; 3) releasing virus producing cells from their arresting at the G2/M period and reducing the ability of producing viruses; 4) interfering with the destruction of bystander cells (for example, dendritic cells, CD8(+) T-cells, NK, (natural killer) cells) on the basis of cell-membrane impairing activities of Vpr, and as a result, such compounds are likely to prevent the reduction of peripheral un-infected CD4(+) T-cells and to suppress the onset of AIDS and the progression of the AIDS state.

In addition, Vpr arresting of the cell cycle is also reproducible by extracellular adding of recombinant Vpr, and in this case, it is reported that addition of the protein at high concentrations induces cell death (apoptosis) in various cells (Finkel, T. H. et. al., Nature Med., 1: 129–134, 1995). It is said that there is on the order of 2–3 nM Vpr in peripheral blood of actual patients with AIDS, and the effect of this secreted Vpr is likely to cause the destruction of bystander cells as described above in 4). Furthermore, it would be likely that the de-regulation of the cell cycle by Vpr promotes canceration of normal cells, and in combination with reduced immune states, leads to the generation of such AIDS-related tumors as Kaposi's sarcoma.

Recently, attention is being focused on accessory proteins as new targets for creating drugs, with accumulating information on physiological functions of accessory proteins. At present, however, there is no medicament targeting an accessory protein such as Vpr.

With respect to Vpr, the situation has been in confusion: it is already known that when Vpr is overexpressed in various cells, the cell cycle is arrested at the G2/M period, whereas there have been reported contradictory results that when weakly expressed, to the contrary, arresting at the G2/M period is not caused, and also apoptosis does not take place with ease. Recently, however, a cell line that resolves such problems has been established, and screening using these cells has demonstrated that a certain flavonoid (quercetin) inhibits Vpr functions (Shimura M. et. al., Biochem. Biophys. Res. Commun. 261: 308–316, 1999).

Kohyo (National Publication of Translated Version) No. Hei 9-511395 (1997) discloses a biologically active peptide fragment of the Vpr protein of HIV, a pharmaceutical composition comprising such a peptide or its biologically active analogue, an antagonist of the peptide, a pharmaceutical composition comprising the antagonist, and a method for treatment and screening using such a compound and a compositions.

The compounds of the formula (1) according to the present invention are known to have an anti-cancer effect and to be useful as a remedy for malignant tumors (International Publication WO95/27699).

DISCLOSURE OF THE INVENTION

An object of the present invention is to provide an excellent anti-HIV agent having a new mechanism of action, that is, to provide an anti-HIV agent that regulates Vpr function to exert an anti-HIV effect.

From the above-described point of view, the present inventors have carried out searching for new anti-HIV agents that target Vpr. More specifically, since cytobiological changes (abnormalities of cell division machinery) observed when aminostilbazole derivatives represented by the following general formula (1) (hereinafter sometimes referred to as the compounds of the present invention) are subjected to action on different cancer cells are closely similar to cell changes observed in cells expressing Vpr, the present inventors have searched about a Vpr function regulating effect of the compound of the present invention. As a result, we have found that the compounds of the present invention have a Vpr function regulating effect, and thus the present invention has been completed.

The present invention relates to a Vpr function regulating agent and an anti-HIV agent, comprising a compound represented by the following general formula [1] or a salt thereof as an active ingredient:

A-B-D-E  [1]

[wherein A represents optionally substituted heteroaryl or an oxide thereof, B represents optionally substituted ethenylene, D represents optionally substituted phenylene, E represents the following formula:

(wherein G represents optionally substituted phenyl, R represents (1) hydrogen, (2) optionally substituted alkyl, (3) optionally substituted alkenyl, (4) alkynyl, or (5) —COR$^0$, R$^0$ represents alkyl, alkoxy, aryloxy, optionally substituted heteroaryl, optionally substituted heteroarylmethyl, or the following formula:

wherein n represents an integer of 1 to 5, R$^5$ and R$^6$ are the same or different and each represents hydrogen, alkyl, hydroxyalkyl, aminoalkyl, or R$^5$ and R$^6$ are taken together with adjacent nitrogen atoms as —NR$^5$(R$^6$) to form optionally substituted cyclic amino, and the cyclic amino may have one oxygen, sulfur or nitrogen atom as annular atoms, in addition to nitrogen atom)].

Preferably, the present invention relates to a Vpr function regulating agent and an anti-HIV agent, comprising the compounds of present invention or the salt thereof as an active ingredient, wherein A is optionally substituted pyridyl or 1-oxide pyridyl, B is non-substituted ethenylene, D is non-substituted or aminoalkoxy-substituted 1,2-phenylene, R of —N(R)—SO$_2$—G as E is alkyl which may be substituted with a substituent selected from the group consisting of halogen, amino, monoalkylamino, dialkylamino, morpholino, alkoxy, hydroxy, cyano, the formula: —CONR$^1$R$^2$ (wherein R$^1$ and R$^2$ are the same or different and each represents hydrogen, hydroxy, alkyl, alkoxy, cycloalkyl, cycloalkyloxy, aryl, aryloxy, aralkyl, aralkyloxy, cycloalkylalkyl, cycloalkylalkyloxy, or tetrahydrofuranyloxy), and the formula: —SO$_2$NR$^3$R$^4$ (wherein R$^3$ and R$^4$ are the same or different and each represents hydrogen or alkyl), alkenyl which may be substituted with halogen, or —COR$^0$, R$^0$ is alkyl, cyclic amino alkyl, or dialkylaminoalkyl, and G is 4-alkoxyphenyl.

More preferably, the present invention relates to a Vpr function regulating agent and an anti-HIV agent, comprising the compounds of present invention or the salt thereof as an active ingredient, wherein A is non-substituted 4-pyridyl or 1-oxide-4-pyridyl, B is ethenylene of a non-substituted trans form, D is non-substituted or aminoalkoxy-substituted 1,2-phenylene, R of —N(R)—SO$_2$-G as E is hydrogen, hydroxyalkyl, or —COR$^0$, R$^0$ is alkyl or morpholinoalkyl or dialkylaminoalkyl, and G is 4-methoxyphenyl.

A feature of the present invention resides in the fact that a Vpr function regulating effect and an anti-HIV effect are found in the compound of the formula [1]. It has never been described in the document and also has never been known that the above compound has these effects.

The present invention will be described in detail below.

Terms used in the present specification and definitions of the respective substituents are as follows.

The term "Vpr function regulating agent" as used herein refers to a drug which enhances or relieves a biological phenomenon caused by Vpr itself, or caused by Vpr as a result of binding with molecules derived from host cells or virus.

The term "anti-HIV agent" as used herein refers to a drug which reduces the viral load by suppressing the growth of HIV or reducing its pathogenicity. Particularly, it refers to a drug which suppresses the destruction of CD4(+) T-cells, other immunocompetent cells in the lymphoid tissue and nerve cells caused by a biological activity of HIV, thereby to suppress the onset of AIDS-related diseases and to relieve the AIDS state.

Examples of "heteroaryl" may include 5- to 6-membered heteroaryl having 1 to 2 nitrogen atoms as an annular atom. Such a heteroaryl may have 1 to 2 substituents at any positions and examples of the substituent may include halogen, alkyl, alkoxy, hydroxy, aminoalkyl and the like. Examples of "heteroaryl" as A may include 6-membered heteroaryl, for example, 2-pyridyl, 3-pyridyl, 4-pyridyl, 2-pyrimidinyl, 4-pyrimidinyl, 5-pyrimidinyl, 3-pyridazinyl, 4-pyridazinyl and pyrazinyl. Among them, non-substituted 4-pyridyl is preferable. Examples of the heteroaryl moiety of "heteroaryl" and "heteroarylmethyl" as R$^0$ may include 5- to 6-membered heteroaryl, for example, 2-pyridyl, 3-pyridyl, 4-pyridyl, 2-pyrimidinyl, 4-pyrimidinyl, 5-pyrimidinyl, 3-pyridazinyl, 4-pyridazinyl, 1-imidazolyl, 2-imidazolyl and 4-imidazoly. Among them, pyridyl is preferable.

"Ethenylene" may have a substituent on the respective atoms and examples of the substituent may include cyano, bromo alkyl and the like. Among them, non-substituted ethenylene is preferable.

Examples of "phenylene" may include 1,2-phenylene, 1,3-phenylene and 1,4-phenylene. Such a phenylene group may have 1 to 2 substituents at any positions and examples of the substituent may include hydroxy, halogen, amino, alkyl, alkoxy, aminoalkyloxy and the like. Non-substituted or aminoalkoxy-substituted 1,2-phenylene is preferable.

"Phenyl" may have 1 to 2 substituents and examples of the substituent may include hydroxy, alkoxy and the like. Among them, alkoxy-substituted phenyl is preferable and 4-methoxyphenyl is particularly preferable.

Examples of "halogen" may include fluorine, chlorine, bromine, iodine and the like.

Examples of "alkyl" may include straight-chain or branched-chain alkyl having 1 to 6 carbon atoms, for example, methyl, ethyl, n-propyl, isopropyl, n-butyl, isobutyl, sec-butyl, tert-butyl, n-pentyl, isopentyl, n-hexyl and isohexyl. Among them, alkyl having 1 to 4 carbon atoms is preferable and methyl is particularly preferable. Alkyl as R may be substituted with a substituent selected from the group consisting of halogen, amino, monoalkylamino, dialkylamino, morpholino, alkoxy, hydroxy, cyano, the formula: —CONR$^1$R$^2$ (wherein R$^1$ and R$^2$ are the same or different and each represents hydrogen, hydroxy, alkyl, alkoxy, cycloalkyl, cycloalkyloxy, aryl, aryloxy, aralkyl, aralkyloxy, cycloalkylalkyl, cycloalkylalkyloxy, or tetrahydrofuranyloxy) and the formula: —SO$_2$NR$^3$R$^4$ (wherein R$^3$ and R$^4$ are the same or different and each represents hydrogen or alkyl).

Examples of the alkyl moiety of "hydroxyalkyl", "monoalkylamino", "dialkylamino", "aminoalkyl", "cycloalkylalkyl" and "cycloalkylalkyloxy" may include "alkyl" described above.

Examples of "alkoxy" may include straight-chain or branched-chain alkoxy having 1 to 6 carbon atoms, for example, methoxy, ethoxy, n-propoxy, isopropoxy, n-butoxy, isobutoxy, sec-butoxy, tert-butoxy, n-pentyloxy, isopentyloxy, n-hexyloxy and isohexyloxy. Among them, alkoxy having 1 to 4 carbon atoms is preferable and methoxy is particularly preferable.

Examples of the alkoxy moiety of "aminoalkoxy" may include "alkoxy" described above.

Examples of "aryloxy" may include optionally substituted aryloxy having 6 to 10 carbon atoms, for example, phenoxy, 1-naphthyloxy and 2-naphthyloxy. Among them, phenoxy is preferable. Examples of the substituent may include alkyl, halogen, hydroxy, alkoxy and the like.

Examples of "alkenyl" may include straight-chain or branched-chain alkenyl having 2 to 6 carbon atoms, for example, vinyl, 1-propenyl, 2-propenyl, isopropenyl, 2-butenyl, 3-butenyl, isobutenyl, metallyl, prenyl, isoprenyl and 1,1-dimethylallyl. Among them, alkenyl having 2 to 4 carbon atoms is preferable. "Alkenyl" as R may be substituted with halogen.

Examples of "alkynyl" may include straight-chain or branched-chain alkynyl having 2 to 6 carbon atoms, for example, ethynyl, 1-propynyl, 2-propynyl, 2-butynyl, 3-butynyl and 3-methyl-2-butynyl. Particularly, alkynyl having 2 to 4 carbon atoms is preferable.

In alkylene represented by "—(CH$_2$)$_n$—" hydrogen atom may be substituted with one amino or alkyl at any positions.

Examples of "cyclic amino" may include 5- to 8-membered cyclic amino, for example, pyrrolidin-1-yl, piperidino, hexamethyleneimino, tetrahydropyridin-1-yl, octahydroazocin-1-yl, piperazin-1-yl, homopiperazin-1-yl, morpholino and thiomorpholino. Such a cyclic amino may have 1 to 2 substituents selected from the group consisting of alkyl, alkenyl, alkynyl, aryl, aralkyl and heterocycle group having a nitrogen atom at any positions. Among them, 5- to 6-membered cyclic amino is preferable, and piperazin-1-yl substituted with pyridyl, non-substituted pyrrolidin-1-yl, piperidino or morpholino is particularly preferable.

Examples of "aryl" may include aryl having 6 to 10 carbon atoms, for example, phenyl, 1-naphthyl and 2-naphthyl.

Examples of "aralkyl" may include aralkyl having 7 to 8 carbon atoms, for example, benzyl and phenethyl.

Examples of the aralkyl moiety of "aralkyloxy" may include those described above.

Examples of "heterocycle having a nitrogen atom" may include cyclic amino and heteroaryl described above. Such a heterocycle may have 1 to 2 substituents selected from the group consisting of alkyl, amino, hydroxy and oxo.

Examples of "cycloalkyl" may include cycloalkyl having 3 to 8 carbon atoms, for example, cyclopropyl, cyclobutyl, cyclopentyl, cyclohexyl, cycloheptyl and cyclooctyl.

Examples of the cycloalkyl moiety of "cycloalkyloxy", "cycloalkylalkyl" and "cycloalkylalkyloxy" may include those described above.

Examples of "salt" of the compounds of the present invention may include pharmacologically acceptable salts, for example, salts with inorganic acids such as hydrochloric acid, sulfuric acid, nitric acid, phosphoric acid, hydrofluoric acid and hydrobromic acid, and salts with organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid and camphorsulfonic acid.

The compounds of the present invention may exist in cis (Z form) and trans (E form) isomers, and each isomer and a mixture thereof are also included in the present invention. Particularly, the E form is preferable.

Examples of the compounds of the present invention may include compounds of the formula [1]. Particularly,
(E)-4-[2-{2-[N-acetyl-N-(4-methoxybenzenesulfonyl)amino]phenyl}ethenyl]pyridine 1-oxide,
(E)-4-[2-{2-[N-acetyl-N-(4-methoxybenzenesulfonyl)amino]phenyl}ethenyl]pyridine,
(E)-4-[2-{2-[N-(4-methoxybenzenesulfonyl)amino]phenyl}ethenyl]pyridine 1-oxide,
(E)-4-[2-{2-[N-(4-methoxybenzenesulfonyl)amino]phenyl}ethenyl]pyridine,
(E)-4-[2-{2-[N-(2-hydroxyethyl)-N-(4-methoxybenzenesulfonyl)amino]phenyl}ethenyl]pyridine 1-oxide,
(E)-4-[2-{2-[N-(2-hydroxyethyl)-N-(4-methoxybenzenesulfonyl)amino]phenyl}ethenyl]pyridine,
(E)-4-[2-{3-(2-aminoethyloxy)-2-[N-(4-methoxybenzenesulfonyl)amino]phenyl}ethenyl]pyridine, and
(E)-4-[2-{3-(2-aminoethyloxy)-2-[N-(4-methoxybenzenesulfonyl)amino]phenyl}ethenyl]pyridine 1-oxide are preferable.

The compounds of the present invention can be produced by the method described in International Publication WO95/27699, International Publication WO01/44195 or Japanese Unexamined Patent Publication No. 2001-261649, or a version thereof.

When the compounds of the present invention are administered as a medicament, they can be administered to a mammal including human as they are or in a mixture with a pharmaceutically acceptable non-toxic inert carrier, for example, as a pharmaceutical composition containing the compound at a level of 0.1% to 99.5%, preferably 0.5% to 90%.

The carrier that can be used includes solid, semi-solid and liquid diluent, filler and other formulation auxiliaries and at least one of them is selectivity employed. The pharmaceutical composition is preferably administered in a unit dosage form. The pharmaceutical composition can be administered into tissue, or orally, intravenously, topically (percutaneously) or rectally. Of course, a dosage form suited for each route of the administration should be used. For example, oral or intravenous administration due to ambulatory is preferable to prevent the progression of the stage of disease in patients in the primary infection stage and the a symptomatic stage, while intravenous administration is preferable for patients in the AIDS state.

The dosage of the compound as a Vpr function regulating agent and an anti-HIV agent may preferably be adjusted in consideration of the patient's factors such as age, body weight, etc., nature and severity of disease, etc., as well as the route of administration, a daily dose as an active ingredient in an adult is usually 0.1 mg to 100 mg per adult, preferably 0.1 mg to 50 mg per adult when given orally, and usually 0.1 mg to 100 mg per adult, preferably 0.1 mg to 50 mg per adult when given intravenously. In some cases, a lower dose may be sufficient or a higher dose may be required. Usually, the dose is given once or several times as being divided into portions, or given intravenously and continuously over a period of 1 to 24 hours a day. When given continuously for a long period (administration in the primary infection stage and the a symptomatic stage), the dose and interval are appropriately controlled after periodically examining the number of peripheral lymphocytes, the amount of virus and the advent of side effects of patients.

Oral administration can be carried out using a solid or liquid unit dosage form, such as a particle, powder, tablet, sugar-coated tablet, capsule, granule, suspension, liquid, syrup, drop, sublingual tablet or other dosage forms.

A particle is produced by pulverizing the compound of the present invention into a suitable particle size. A powder is produced by pulverizing the compound of the present invention into a suitable particle size followed by mixing with a pharmaceutical carrier, such as an edible carbohydrate including starches or mannitol, which has also been pulverized into a suitable particle size. Those that may be added if necessary are flavors, preservatives, dispersing agents, colorants, fragrances and the like.

A capsule is produced by filling a particle or powder which has been pulverized as described above or a granule obtained as described in the section of a tablet for example in a capsule such as a gelatin capsule. It is also possible that an additive such as a lubricant, fluidizing agent, such as colloidal silica, talc, magnesium stearate, calcium stearate or solid polyethylene glycol is mixed with the pulverized material prior to the filling procedure. The efficacy of the drug after ingestion of capsule may be improved by adding a disintegrator or solubilizer, such as carboxymethyl cellulose, calcium carboxymethyl cellulose, low substituted hydroxypropyl cellulose, sodium croscarmellose, sodium carboxymethyl starch, calcium carbonate or sodium carbonate, may be added.

The finely pulverized powder may be suspended and dispersed in a vegetable oil, polyethylene glycol, glycerin and surfactant, and then encapsulated in a gelatin sheet, thereby obtaining a soft capsule.

A tablet can be produced by preparing a powdery composition by adding an excipient, granulating or slugging it, adding a disintegrator or lubricant thereto, and then compact into a tablet. The powdery composition can be produced by mixing an appropriately pulverized material with a diluent or base described above if necessary together with a binder (for example, sodium carboxymethyl cellulose, methyl cellulose, hydroxypropylmethyl cellulose, gelatin, polyvinyl pyrrolidone and polyvinyl alcohol), a dissolution retardant (for example, paraffin), a resorption promoter (for example, quaternary salt), or an adsorbent (for example, bentonite, kaolin and calcium diphosphate). The powdery composition can be granulated by wetting with a binder such as a syrup, starch glue, gum arabic, cellulose solution or polymer solution, followed by mixing with stirring, drying and grinding. Instead of the procedure for granulating a powder as described above, another procedure may be employed in which a mix is subjected first to a tablet compacting machine to form a morphologically incomplete slug which is then ground. A granule thus obtained may contain, as a lubricant, stearic acid, stearates, talc, mineral oil and the like, for the purpose of preventing any adhesion with each other. The mixture thus lubricated is then compacted into tablets. A plane tablet thus obtained may be film-coated or sugar-coated.

The compounds of the present invention may be mixed with a fluidized inert carrier and then compacted directly into tablets without being subjected to the granulating or slugging process as described above. A transparent or semi-transparent protective film in the form of a shellac sealing film, a film of a sugar or polymeric material and a glossy film of a wax may also be employed. Other oral dosage forms, such as a solution, syrup and elixir can be formulated as a unit dosage form whose certain amount contains a certain amount of a medicament. A syrup is produced by dissolving the compound of the present invention in an appropriate flavored aqueous solution, while an elixir is produced by using a non-toxic alcoholic carrier. A suspension is formulated by dispersing the compound of the present invention in a non-toxic carrier. Additives such as a solubilizing agent, an emulsifier (for example ethoxylated isostearyl alcohols, polyoxyethylene sorbitol esters), a preservative, a flavor (for example, peppermint oil and saccharin) and the like may be added, if necessary.

An oral unit dosage formulation may also be a microcapsule if desired. Such a formulation may also be coated or embedded in a polymer, wax or the like to obtain a prolonged activity or sustained release of the active ingredient.

In parenteral administration, an injection, a suppository and the like can be used. Parenteral administration can be accomplished by using a liquid unit dosage form, such as a solution or suspension, for subcutaneous, intramuscular or intravenous administration. Such a unit dosage form can be produced by suspending or dissolving predetermined amount of the compound of the present invention in a non-toxic liquid carrier such as an aqueous or oily medium compatible with the purpose of the injection followed by sterilizing the suspension or solution. It is also possible to add a non-toxic salt or salt solution for the purpose of making an injection solution isotonic. It is also possible to use a stabilizer, preservative, emulsifier and the like.

A rectal administration can be accomplished by using a suppository produced by dissolving or suspending the compounds of the present invention in a water-soluble or water-insoluble solid having a low melting point such as a polyethylene glycol, cocoa butter, semi-synthesized fats and fatty oils (for example, Witepsol (R)), higher esters (for example, myristyl palmitate) as well as a mixture thereof.

In the medicament of the present invention, it is possible to use in combination with other ingredients, for example, reverse transcriptase inhibitors and virus protease inhibitors inherent to HIV.

BRIEF DESCRIPTION OF THE DRAWINGS

FIG. 1 shows in vitro functional antagonism between a flavonoid (quercetin) and the compound B. A is a copy of a photograph showing the results when microscopic observations were made of control (untreated) cells; B, cells treated for 72 hours with the compound B (600 nM) described below; C, cells pretreated with 1.0 µM quercetin for 48 hours, followed by treatment with the compound B (600 nM) for 72 hours. ×4 and ×20 represent a magnification of 4× and 20×, respectively.

FIG. 2 (1) shows electrophoresis views of purified FLAG-fused Vpr protein: (a) a picture of the gel stained with Coomassie Blue, (b) Western blot with an anti-FLAG antibody. FIG. 2 (2) shows direct binding of the compound and Vpr: lane 1, radioisotope-labeled FLAG-fused Vpr; lane 2, precipitation of radioisotope-labeled FLAG-fused Vpr with beads not having the compound immobilized thereto (control); lane 3, precipitation of radioisotope-labeled FLAG-fused Vpr with beads having the compound immobilized thereto; lane 4, radioisotope-labeled FLAG-fused VprΔC; lane 5, precipitation of radioisotope-labeled FLAG-fused VprΔC with beads having the compound immobilized thereto.

FIG. 3 (1) shows the inhibition of cytotoxic activity of Vpr by the compound, which is indicated by detecting (PI staining) dead cells on a flow cytometer. The compound concentration is 0 nM in (a), 0.1 nM in (b), and 1.0 nM in (c). The ordinate axis represents the number of counts and the abscissa axis represents the intensity of fluorescence. FIG. 3 (2) shows copies of photographs showing the results when microscopic observations were made of the state in which the compound removes the inhibition of cell proliferation induced by purified FLAG-fused Vpr. The compound concentration is 0.1 nM in (a), 1.0 nM in (b), and 10.0 nM in (c).

BEST MODE FOR CARRYING OUT THE INVENTION

The present invention will now be described in more detail with reference to Production Examples of typical starting materials (Reference Examples), Production Examples of the compounds of the present invention (Examples), Pharmaceutical Preparation Examples and Test Examples, but the present invention is not limited thereto. The specific rotation was measured at 20° C. In the Test Examples, (E)-4-[2-{2-[N-(4-methoxybenzenesulfonyl)amino]phenyl}ethenyl]pyridine 1-oxide (hereinafter referred to as a compound A) and (E)-4-[2-{3-(2-aminoethyloxy)-2-[N-(4-methoxybenzenesulfonyl)amino]phenyl}ethenyl]pyridine (hereinafter referred to as a compound B) were used. In the Formulation Examples, the compound A and (E)-4-{2-[2-{N-(4-methoxybenzenesulfonyl)-N-[4-(2-pyridyl)piperadino]acetylamino}phenyl]ethenyl}pyridine 1-oxide dihydrochloride (hereinafter referred to as a compound 2) were used.

REFERENCE EXAMPLE 1

Production of (E)-2-(2-tert-butoxycarbonylaminoethoxy)-6-[2-(4-pyridyl)ethenyl]aniline (Step 1) Synthesis of 3-hydroxy-2-nitrobenzaldehyde 3.62 g of 3-methoxy-2-nitrobenzaldehyde was dissolved in 80 ml of methylene chloride and a boron tribromide-methylene chloride solution (15.03 g of boron tribromide, 40 ml of methylene chloride) was added dropwise under ice cooling, followed by stirring at 0° C. for one hour. The reaction solution was poured into ice, extracted with chloroform, dried and then concentrated to obtain 3.32 g of the desired compound.

(Step 2) Production of (E)-2-acetoxy-6-[2-(4-pyridyl)ethenyl]nitrobenzene

To 3.17 g of the compound obtained in the step 1, 1.94 g of 4-picoline and 4.79 g of acetic anhydride were added, and then the mixture was refluxed with stirring for 12 hours. The reaction solution was poured into ice, neutralized with potassium carbonate, extracted with chloroform and then dried over magnesium sulfate. After the solvent was distilled off under reduced pressure, the residue was subjected to silica gel column chromatography (CHCl$_3$) to obtain 4.78 g of the desired compound.

(Step 3) Production of (E)-2-hydroxy-6-[2-(4-pyridyl)ethenyl]nitrobenzene 4.54 g of the compound obtained in the step 2 was dissolved in 160 ml of methanol and 4.42 of potassium carbonate was added, followed by stirring at room temperature for 2 hours. After the reaction solution was concentrated, the residue was combined with iced water and neutralized with 2 N-hydrochloric acid and then the deposited crystal was collected by filtration to obtain 3.47 g of the desired compound. The resulting compound was used as a material without purification.

(Step 4) Production of (E)-2-(2-tert-butoxycarbonylaminoethoxy)-6-[2-(4-pyridyl) ethenyl]nitrobenzene 2.18 g of the compound obtained in the step 3 was dissolved in 9 ml of DMSO and 0.54 g of 60% sodium hydride was added under an argon gas flow, followed by stirring at room temperature for one hour. 4.63 g of 2-bromoethyl-tert-butoxycarbonylamine was added, followed by stirring with heating at 120° C. for 3 hours. The reaction solution was poured into iced water, combined with ethyl acetate, washed with water (3 times), washed with saturated brine and then dried over magnesium sulfate. After the solvent was distilled off under reduced pressure, the residue was subjected to silica gel column chromatography (CHCl$_3$:MeOH=50:1) to obtain 1.90 g of the desired compound.

(Step 5) Production of (E)-2-(2-tert-butoxycarbonylaminoethoxy)-6-[2-(4-pyridyl)ethenyl]aniline 1.90 g of the compound obtained in the step 4 was dissolved in 50 ml of 70% hydrous methanol and 4.90 g of reduced iron and 0.30 g of calcium chloride were added, and then the mixture was refluxed with stirring for 4 hours. After the reaction solution was filtered through celite, the filtrate was concentrated and the residue was subjected to silica gel column chromatography (CHCl$_3$:MeOH=50:1) to obtain 1.45 g of the desired compound.

EXAMPLE 1

(E)-4-[2-{2-[N-phenoxycarbonyl-N-(4-methoxybenzenesulfonyl)amino]phenyl}ethenyl]pyridine 1.00 g of (E)-4-[2-{2-[N-(4-methoxybenzenesulfonyl)amino]phenyl}ethenyl]pyridine was suspended in 40 ml of chloroform and, after adding 1.82 g of phenyl chlorocarbonate, 1.20 g of triethylamine was slowly added under ice cooling. Then, the mixture was stirred at room temperature for 5 minutes. The solvent was distilled off under reduced pressure and the desired product was purified by silica gel column (carrier: Wako Gel C200, developing solvent chloroform) to obtain the desired compound. The desired compound was treated with ethanol to obtain 0.71 g of a white granular crystal.

Elemental analysis (for $C_{27}H_{22}N_2O_5S$) Calcd. (%): H, 4.55; C, 66.65; N, 5.75 Found (%): H, 4.51; C, 66.44; N, 5.67

In the same manner, the following desired compounds were synthesized.

EXAMPLE 2

(E)-4-[2-{2-[N-methoxycarbonyl-N-(4-methoxybenzenesulfonyl)amino]phenyl}ethenyl]pyridine Elemental analysis (for $C_{22}H_{20}N_2O_5S$) Calcd. (%): H, 4.75; C, 62.25; N, 6.60 Found (%): H, 4.83; C, 61.97; N, 6.51

EXAMPLE 3

(E)-4-[2-{2-[N-ethoxycarbonyl-N-(4-methoxybenzenesulfonyl)amino]phenyl}ethenyl]pyridine Elemental analysis (for $C_{23}H_{22}N_2O_5S \cdot \frac{1}{3}H_2O$) Calcd. (%): H, 5.11; C, 62.49; N, 6.34 Found (%): H, 5.09; C, 62.39; N, 6.34

EXAMPLE 4

(E)-4-[2-{2-[N-n-propoxycarbonyl-N-(4-methoxybenzenesulfonyl)amino]phenyl}ethenyl]pyridine hydrochloride Elemental analysis (for $C_{24}H_{24}N_2O_5S \cdot HCl \cdot \frac{1}{2}H_2O$) Calcd. (%): H, 5.26; C, 57.88; N, 5.63 Found (%): H, 5.23; C, 58.12; N, 5.72

EXAMPLE 5

(E)-4-[2-{2-[N-n-butoxycarbonyl-N-(4-methoxybenzenesulfonyl)amino]phenyl}ethenyl]pyridine hydrochloride Elemental analysis (for $C_{25}H_{26}N_2O_5S \cdot HCl \cdot \frac{1}{2}H_2O$) Calcd. (%): H, 5.51; C, 58.64; N, 5.47 Found (%): H, 5.47; C, 58.44; N, 5.49

EXAMPLE 6

(E)-4-[2-{3-(2-aminoethoxy)-2-[N-(4-methoxybenzenesulfonyl)amino]phenyl}ethenyl]pyridine dihydrochloride (Step 1) Production of (E)-4-[2-{3-(2-tert-butoxycarbonylaminoethoxy)-2-[N-(4-methoxybenzenesulfonyl)amino]phenyl}ethenyl]pyridine 1.42 g of (E)-2-(2-tert-butoxycarbonylaminoethoxy)-6-[2-(4-pyridyl)ethenyl]aniline obtained in the step 5 of Reference Example 3 was dissolved in 14 ml of pyridine and 0.99 g of 4-methoxybenzenesulfonyl chloride was added, followed by stirring at room temperature overnight. The reaction solution was concentrated and the residue was combined with iced water, extracted with chloroform and then dried over magnesium sulfate. After the solvent was distilled off under reduced pressure, the residue was subjected to silica gel column chromatography ($CHCl_3$: MeOH=30:1) to obtain 2.19 g of the desired compound.

(Step 2) Production of (E)-4-[2-{3-(2-tert-butoxycarbonylaminoethoxy)-2-[N-(4-methoxybenzenesulfonyl)amino]phenyl}ethenyl]pyridine 1-oxide 0.56 g of the compound obtained in the step 1 was dissolved in 5 ml of chloroform and m-chloroperbenzoic acid was added, followed by stirring at room temperature for one hour. The reaction solution was washed with water three times and then dried over magnesium sulfate. After the solvent was distilled off under reduced pressure, the residue was subjected to silica gel column chromatography ($CHCl_3$: MeOH=20:1) to obtain 0.46 g of the desired compound.

(Step 3) 2.10 g of the compound obtained in the step 2 was dissolved in 10 ml of methylene chloride and 10.5 ml of trifluoroacetic acid was added dropwise under ice cooling, followed by stirring at room temperature for 2 hours. The reaction solution was combined with iced water, made weak basic by the addition of potassium carbonate, extracted with chloroform and then dried over magnesium sulfate. After the solvent was distilled off under reduced pressure, the residue was subjected to silica gel column chromatography ($CHCl_3$: MeOH=20:1) to obtain 1.33 g of a free form.

The free form was dissolved in 20 ml of methanol and an excess amount of a 20% hydrochloric acid-ether solution was added under ice cooling, followed by stirring for one hour. The reaction solution was concentrated and treated with ethanol to obtain 1.30 g of the desired compound (pale yellow crystal).

Elemental analysis (for $C_{22}H_{23}N_3O_4S \cdot 2HCl \cdot H_2O$) Calcd. (%): C, 51.17; H, 5.27; N, 8.14 Found (%): C, 51.04; H, 4.99; N, 8.02

EXAMPLE 7

(E)-4-[2-{3-(2-aminoethoxy)-2-[N-(4-methoxybenzenesulfonyl)amino]phenyl}ethenyl]pyridine 1-oxide dihydrochloride 2.38 g of the compound obtained in the step 2 of Example 6 was dissolved in 23 ml of methylene chloride and 23 ml of trifluoroacetic acid was added dropwise under ice cooling, followed by stirring at room temperature for 2 hours. The reaction solution was combined with iced water, made weak basic by the addition of potassium carbonate, extracted with chloroform and then dried over magnesium sulfate. After the solvent was distilled off under reduced pressure, the residue was subjected to silica gel column chromatography ($CHCl_3$: MeOH:28% $NH_3$ (aq.)=90:10:1) to obtain 1.48 g of a free form.

The free form was dissolved in 50 ml of methanol and an excess amount of a 20% hydrochloric acid-ether solution was added under ice cooling, followed by stirring for one hour. The reaction solution was concentrated and treated with ethanol to obtain 1.50 g of the desired compound (pale yellow crystal).

Elemental analysis (for $C_{22}H_{23}N_3O_5S \cdot 2HCl \cdot 0.3H_2O$) Calcd. (%): C, 50.83; H, 4.96; N, 8.08 Found (%): C, 50.86; H, 4.88; N, 7.99

FORMULATION EXAMPLE 1

180 mg Per Tablet for Internal Use

| | |
|---|---|
| Compound A | 10 mg |
| Lactose | 100 mg |
| Corn starch | 55 mg |
| Low substituted hydroxypropyl cellulose | 9 mg |
| Polyvinyl alcohol (partially saponified product) | 5 mg |
| Magnesium stearate | 1 mg |

The above ingredients are weighed in accordance with the formulation. The ingredients, excluding polyvinyl alcohol and magnesium stearate, are uniformly mixed and tabletting granules are produced by a wet granulation method using an aqueous polyvinyl alcohol solution as a binder. After mixing the tabletting granules with magnesium stearate, the mixture is subjected to a tablet compacting machine to mold into tablets each 8 mm in diameter weighing 180 mg per tablet, thereby obtaining a tablet for internal use.

FORMULATION EXAMPLE 2

220 mg Per Hard Capsule

| | |
|---|---|
| Compound A | 10 mg |
| Lactose | 187 mg |
| Microcrystalline cellulose | 20 mg |
| Magnesium stearate | 3 mg |

The above ingredients are weighed in accordance with the formulation and, after mixing uniformly, 220 mg of the mixture is filled into a #2 capsule using a capsule filling machine, thereby obtaining a hard capsule.

FORMULATION EXAMPLE 3

1 g Per Granule

| | |
|---|---|
| Compound A | 10 mg |
| Lactose | 880 mg |
| Low substituted hydroxypropyl cellulose | 70 mg |
| Hydroxypropyl cellulose | 40 mg |

The above ingredients are weighed in accordance with the formulation and, after mixing and kneading uniformly, the kneaded mixture is subjected to a granulating machine to mold into granules each 0.7 mm in diameter, thereby obtaining a granule.

FORMULATION EXAMPLE 4

1 ml Per Injection

| | |
|---|---|
| Compound 2 | 10 mg |
| Mannite | 50 mg |
| Water for injection | q.s. |

(Compound 2 is (E)-4-{2-[2-{N-(4-methoxybenzene-sulfonyl)-N-[4-(2-pyridyl)piperadino]acetylamino}phenyl]ethenyl}pyridine1-oxide dihydrochloride)

Preparation Method

After the compounds of the present invention and mannite are dissolved in water for injection, the resulting solution is aseptically filtered through a membrane filter (pore size: 0.22 μm). After filling into a vial, the vial is subjected to freeze-drying to obtain an injection to be dissolved before using.

FORMULATION EXAMPLE 5

1 ml Per Injection

| | |
|---|---|
| Compound 2 | 10 mg |
| Maltose | 100 mg |
| Water for injection | q.s. |

Preparation Method

After the compounds of the present invention and maltose are dissolved in water for injection, the resulting solution is aseptically filtered through a membrane filter (pore size: 0.22 μm). After filling into a vial, the vial is subjected to freeze-drying to obtain an injection to be dissolved before using.

TEST EXAMPLE 1

In Vitro Functional Antagonism Between Flavonoid (Quercetin) and Compound B

Figure 1:
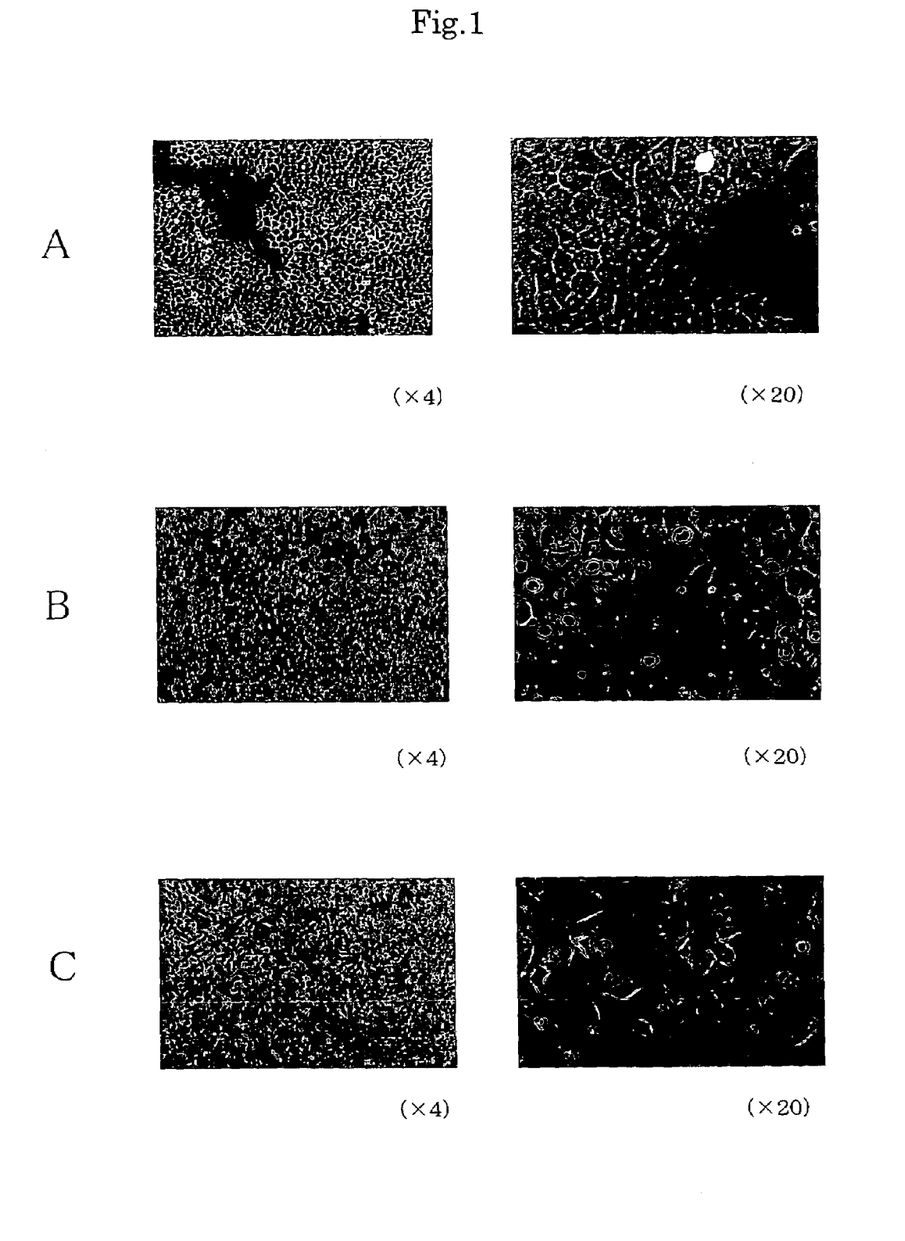

Three types of cells were employed (HeLa, ECV304, and HBL-100, purchased from ATCC), and for each type, $1 \times 10^5$ cells were seeded in a 10 cm dish and cultured in D-MEM/F-12 medium (Gibco BRL) for 18–20 hours. On the next day, the medium was changed to the same medium containing 1.0 μM quercetin (Sigma; hereinafter abbreviated to QCT), followed by culturing for an additional 2 days. The compound A was then added at a concentration of 600 nM, and 72 hours later observations under a microscope were made of cell morphologies. As a representative example, FIG. 1 shows the results obtained when HeLa cells were employed. Similar results were obtained when the other types of cells were employed.

As is obvious from FIG. 1, in the cell group receiving only the treatment with the present compound (FIG. 1, B), the cell cycle is arrested at the G2/M period, many cells which became globular are visible, and the number of multinucleate cells having plural nuclei within single cells are apparently increased, also for cells adhered onto culturing dishes, compared with the control group (FIG. 1, A). On the other hand, in the cell group subjected to the pre-treatment with quercetin, a Vpr inhibitor, effects of the compound as described above disappear almost completely (FIG. 1, C). These results reveal that the present compound results in functional antagonism with quercetin.

TEST EXAMPLE 2

In Vitro Direct Binding of Vpr and Compound

1) Preparation of a Vpr Gene Fused to N-Terminal FLAG (SEQ ID NO:1)

A Vpr gene fused to N-terminal FLAG (SEQ ID NO:1) was obtained by PCR (polymerase chain reaction) using as a template pBT-1 (purchased from ATCC) into which the HIV genome without env had been incorporated. Primers utilized were synthetic DNAs having the following sequences (SEQ ID NOs:1 and 2). N-terminal FLAG: Asp Tyr Lys Asp Asp Asp Asp Lys (SEQ ID NO:1);

```
5'-primer:
5'-CTCCCTCGAGGGCACCATGGACTATAAGGACGA (SEQ ID NO: 2)

CGACGACAACATGGAACAAGCCCCAGAAGACC-3';

3'-primer:
5'-CTTTCTAGACTAGGATCTACTGGCTCCATTTC- (SEQ ID NO: 3)

3'.
```

The DNA fragment of interest (300 bp) was recovered from PCR reaction products by agarose gel electrophoresis, and then cloned into the pGEM-T vector (Promega). This fragment was base analyzed on both plus and minus strands and was verified to correspond to the intended fused Vpr. The vector into which the Vpr gene fused to FLAG has been incorporated is hereinafter referred to as pGEM-T/Vpr-wt. Furthermore, using this pGEM-T/Vpr-wt as a template, a second Vpr gene fused to FLAG in which a C-terminal region of Vpr (a.a. 73–96) was deleted was obtained by PCR utilizing primers shown below (SEQ ID Nos:4 and 5).

```
5'-primer:
5'-TCTCCCTCGAGGGCACCATGGACTATAAG-    (SEQ ID NO: 4)

3';

3'-primer:
5'CGACATCTAGACTAGAAATGGATAAACAGCA    (SEQ ID NO: 5)

GTTG.
```

This fused gene was cloned into the pGEM-T vector as described above, and the resulting vector is hereinafter referred to as pGEM-T/VprΔC.

2) Preparation of Agarose Beads Having Compound Immobilized Thereto

One milligram of the compound B was dissolved in 1 ml of 50% DMSO (dimethyl sulfoxide), and to this NHS (N-hydroxysuccimide)-activated Sepharose 4 FF (Amersham-Pharmacia Biotech) of a bed volume of 2 ml was added and subjected to reaction at room temperature for 2 hours with shaking. After the reaction, a 2M Tris solution (pH 8.0) was added and allowed to stand at 4° C. overnight, followed by washing, and a 50% suspension in PBS was prepared for experiments.

3) Preparation of FLAG-fused Vpr

Preparation of FLAG-fused Vpr was performed by transcription and translation from the T7 promoter employing the TNT-coupled wheat germ extract in vitro transcription/translation system (wheat germ extract transcription/translation system) (Promega). Specifically, 1.0 μg of pGEM-T/Vpr-wt (or pGEM-T/VprΔC) digested with a restriction enzyme PstI was transcribed and translated with T7 RNA polymerase in 25 μl of the wheat germ extract in the presence of 100 μCi of $^{35}$S-methionine. Whether these products were Vpr was analyzed by carrying out western blotting according to typical procedures employing an anti-FLAG antibody after samples resulting from transcription and translation in the absence of the radiolabel were denatured with SDS (sodium dodecylsulfate).

4) Affinity Precipitation

Observations of direct binding of the compound B and the FLAG-fused Vpr (or FLAG-fused VprΔC) were made by mixing Sepharose beads having the compound B immobilized thereto and the FLAG-fused Vpr (or FLAG-fused VprΔC), followed by collecting the beads and identifying co-precipitation with Vpr.

Figure 2:
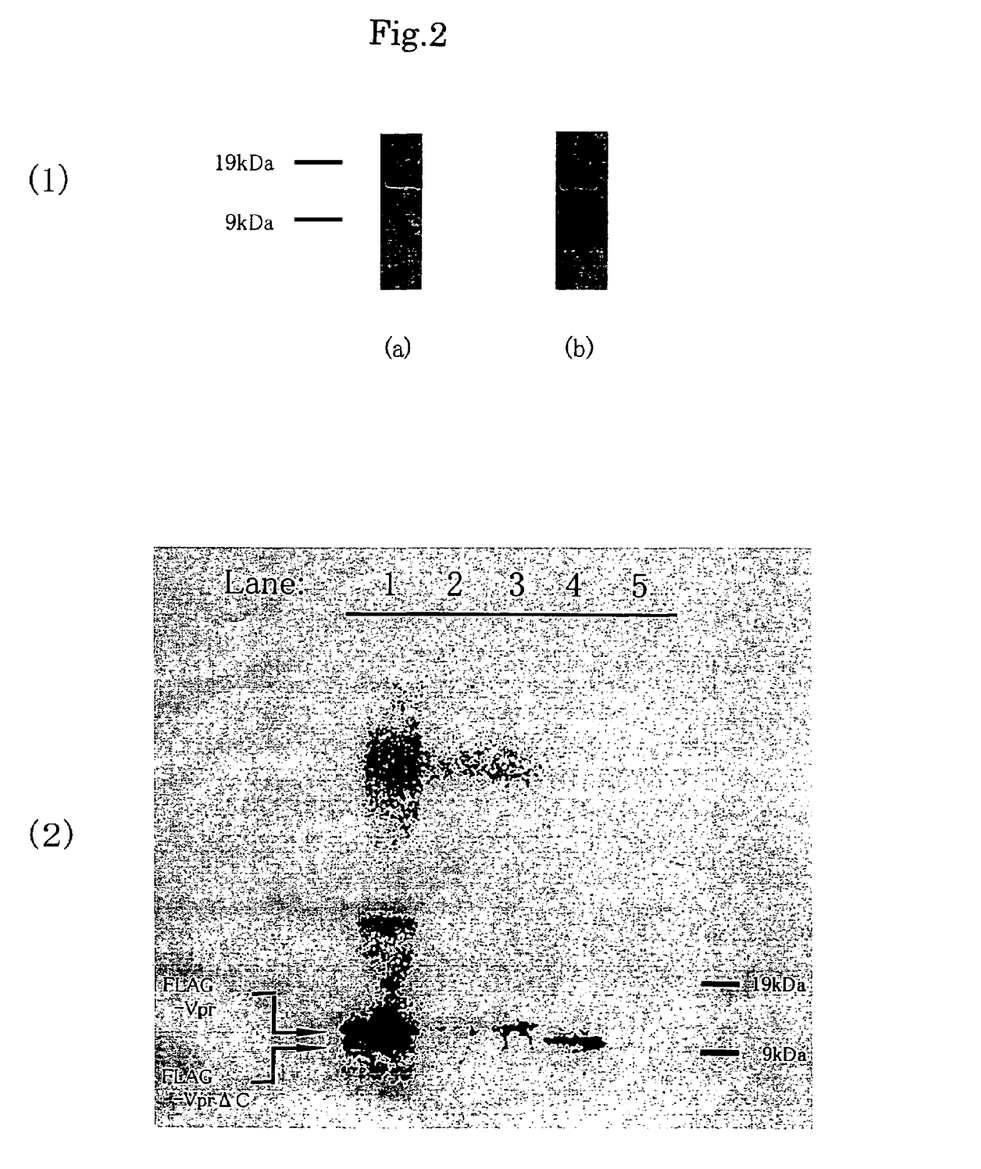
Figure 3:
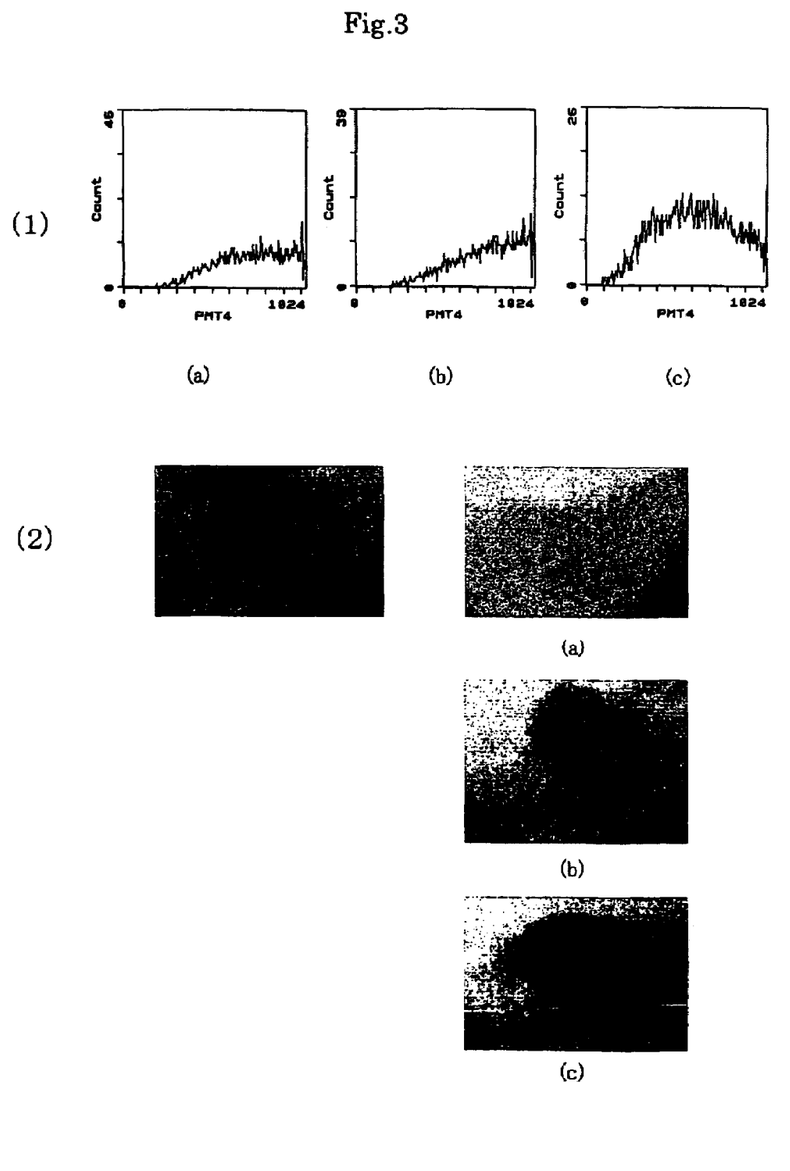

10 μl of a reaction solution containing the radiolabeled FLAG-fused Vpr (or FLAG-fused VprΔC), 10 μl (bed volume) of Sepharose beads having the compound B immobilized thereto, and 10 μl of PBS were mixed and the mixture was gently stirred at room temperature for 2 hours or at 4° C. overnight. The Sepharose beads were then washed 3 times or more with PBS containing 0.1% Brij (Sigma), and SDS denature was carried out, followed by acrylamide gel electrophoresis. After drying the gel, analysis was performed on a BAS 2000 Image Analyzer (Fuji Photo Film Co., Ltd.). The results are shown in FIG. 2.

As shown in FIG. 2 (2), there were observed bands of molecules which seemed to be FLAG-fused Vpr and FLAG-fused VprΔC produced in the wheat germ extract transcription/translation system (lanes 1 and 4). Both bands displayed the mobility corresponding with the predicted molecular weight. Also, the results from western blotting employing an anti-FLAG antibody revealed that the molecules corresponding to these bands have a FLAG epitope. From the results of affinity precipitation, FLAG-fused Vpr was observed to bind to the compound-immobilized beads (lane 3), whereas FLAG-fused VprΔC having the C-terminal deleted was not observed to bind to the beads (lane 5). From these results, it has turned out that the compound B binds directly to the C-terminal region which is believed to be important to Vpr effects of arresting the cell cycle and cytotoxicity.

TEST EXAMPLE 3

Inhibition of Vpr Cytotoxic Activity by Compound

1) Mass Purification of FLAG-fused Vpr

An E. coli strain DH5α transformed with pGEM-T/Vpr-wt was cultured overnight at 37° C. in 60 ml of LB medium containing 0.5% glucose as pre-culture. On the next day, 30 ml aliquots of this culture were added to one-liter LB mediums containing 0.5% glucose, which in turn were cultured at 37° C., and to which, at the time of reaching an $OD_{600}$ of 0.6, IPTG (isopropyl-β-D-thiogalactopyranoside) was added at 0.1 mM and culturing was continued for an additional two hours. Cells were then harvested by centrifugation. Cells were suspended in a lysis solution [10 mM Tris-HCl (pH 7.5), 2% CHAPS (3-[(3-cholamidopropyl) dimethylammonio]propanesulfonic acid),2% n-octyl-β-D-glucoside(both from Dojindo), 1M NaCl, 10 μM PMSF (phenylmethylsulfonyl fluoride)] and then dispersed with an electric homogenizer for 5 minutes and by 10 strokes in a Teflon homogenizer, followed by further processing with a ultrasonificator on ice for 5 minutes. Supernatant was collected by low-speed centrifugation (8000 g, 20 minutes), and this supernatant was subjected further to high-speed centrifugation (50000 g, 20 minutes) to obtain its supernatant. The supernatant was passed through a filter having a pore size of 2 μm and then diluted 4 times or more in 10 mM Tris (pH 7.5), 10 μM PMSF, to which 2 ml (bed volume) of anti-FLAG-antibody immobilized agarose beads was added, followed by mixing overnight at 4° C. with stirring. On the next day, the beads were collected, washed 3 times with TBST, and then suspended in 1 ml TBST containing 100 μM of FLAG peptide (Sigma) and stirred overnight to elute FLAG-fused Vpr from the beads. The eluate was dialyzed to reduce CHAPS and the concentration of n-octyl-β-D-glucoside to 0.05%, and then concentrated about 5 times with a Centricon (Amicon).

The obtained protein run together with lysozyme having almost the same molecular weight (a molecular weight of 19 kDa; Gibco-BRL), and its amount was calculated by comparing the staining intensity of the bands stained with Coomassie Blue.

2) Suppression Effects of the Compound on Cytotoxic Activity of FLAG-fused Vpr

FIG. 2 (1) shows an electrophoresis image of purified FLAG-fused Vpr (stained with Coomassie Blue). Western blotting confirmed that an anti-FLAG antibody recognizes this molecule.

Test 1: HeLa cells were cultured in 6 cm dishes. At a confluency (saturation) of about 30%, 1 μM of FLAG-fused Vpr and different concentrations of the compound were added, and culturing was done for 48 hours. After culturing, PI (propidium iodide) was added into the medium for staining, and cells were treated with trypsin and collected. Cells were analyzed on a flow cytometer and the percentage of PI-stained dead cells was determined. As shown in FIG. 3 (1), it has turned out that the compound reduces the number of dead cells in a dose dependent manner.

Test 2: Jurkat T-cells were plated at a density of $2\times10^5$ cells/ml in 24-well plates, into which FLAG-fused Vpr was added at a concentration of 1 μM. Different concentrations of the compound were further added, and culturing was carried out at 37° C. for 48 hours, followed by counting the number of cells. This experiment was repeated three times and the average percentage of inhibiting the growth was calculated.

As shown in FIG. 3 (2), the presence of FLAG-fused Vpr inhibited the growth by 30%, whereas the coexistence with 10 nM of the compound resulted in reducing the suppression of growth to 13%.

From the results of the above-described Test Examples 1 to 3, the present compound inhibits the cytotoxic activity of Vpr at a concentration (10 nM) at which it does not display a significant anti-cancer activity. It is known that the present compound has low toxicity and high safety.

INDUSTRIAL APPLICABILITY

The present compound is a superior agent for regulating Vpr functions, and inhibits the destruction of various cells based on HIV infection, and therefore can be employed as an agent for preventing the onset of and treating AIDS. Although it is reported that extracellular addition of Vpr promotes the production of viruses from persistent infection cells, it is also possible that the present compound suppresses this and retains persistent infection. Molecules functionally equivalent to Vpr have not been fully identified at present, but the present compound also could find applications as a treating agent for human adult T-cell leukemia, an infectious disease caused by another human pathogenic retrovirus HTLV-1.

The invention claimed is:

1. A method of treating HIV infection or AIDS comprising administering to a subject infected with HIV or a subject with AIDS an effective amount of a composition comprising an aminostilbazole derivative represented by the following formula [1] or a salt thereof:

A-B-D-E-      [1]

wherein A represents optionally substituted pyridyl or 1-oxide pyridyl, B represents optionally substituted ethenylene, D represents optionally substituted phenylene, E represents the following formula:

wherein G represents optionally substituted phenyl, R represents (1) hydrogen, (2) optionally substituted alkyl, (3) optionally substituted alkenyl, (4) alkynyl, or (5)-$COR^0$, $R^0$ represents alkyl, alkoxy, aryloxy, or the following formula:

wherein n represents an integer of 1 to 5, $R^5$ and $R^6$ are the same or different and each represents hydrogen, alkyl, hydroxyalkyl or aminoalkyl.

2. The method according to claim 1, wherein A is optionally substituted pyridyl or 1-oxide pyridyl, B is non-substituted ethenylene, D is non-substituted or aminoalkoxy-substituted 1,2-phenylene, R of —N(R)—$SO_2$—G as E is alkyl which may be substituted with a substituent selected from the group consisting of halogen, amino, monoalkylamino, dialkylamino, morpholino, alkoxy, hydroxy, cyano, the formula: —$CONR^1R^2$ (wherein $R^1$ and $R^2$ are the same or different and each represents hydrogen, hydroxy, alkyl, alkoxy, cycloalkyl, cycloalkyloxy, aryl, aryloxy, aralkyl, aralkyloxy, cycloalkylalkyl, cycloalkylalkyloxy, or tetrahydrofuranyloxy), and the formula: —$SO_2NR^3R^4$ (wherein $R^3$ and $R^4$ are the same or different and each represents hydrogen or alkyl), alkenyl which may be substituted with halogen, or —$COR^0$, $R^0$ is alkyl, or dialkylaminoalkyl, and G is 4-alkoxyphenyl.

3. The method according to claim 1, wherein A is non-substituted 4-pyridyl or 1-oxide-4-pyridyl, B is ethenylene of a non-substituted trans form, D is non-substituted or aminoalkoxy-substituted 1,2-phenylene, R of —N(R)—$SO_2$—G as E is hydrogen, hydroxyalkyl, or —$COR^0$, $R^0$ is alkyl or dialkylaminoalkyl, and G is 4-methoxyphenyl.

4. The method according to claim 1, wherein the compound represented by the formula [I] is a compound selected from the group consisting of (E)-4-[2-{2-[N-acetyl-N-(4-methoxybenzenesulfonyl)amino]phenyl}ethenyl]pyridine 1-oxide, (E)-4-[2-{2-[N-acetyl-N-(4-methoxybenzenesulfonyl)amino]phenyl}ethenyl]pyridine, (E)-4-[2-{2-[N-(4-methoxybenzenesulfonyl)amino]phenyl}ethenyl]pyridine 1-oxide, (E)-4-[2-{2-[N-(4-methoxybenzenesulfonyl)amino]phenyl}ethenyl]pyridine, (E)-4-[2-{2-[N-(2-hydroxyethyl)-N-(4-methoxybenzenesulfonyl)amino]phenyl}ethenyl]pyridine 1-oxide, (E)-4-[2-{2-[N-(2-hydroxyethyl)-N-(4-methoxybenzenesulfonyl)amino]phenyl}ethenyl]pyridine, (E)-4-[2-{3-(2-aminoethyloxy)-2-[N-(4methoxybenzenesulfonyl)amino]phenyl}ethenyl]pyridine, and (E)-4-[2-{3-(2-aminoethyloxy)-2-[N-(4-methoxybenzenesulfonyl)amino]phenyl}ethenyl]pyridine 1-oxide.

5. A method for negative regulation of Vpr function in vitro, which comprises administering to cells infected with HIV in need of such negative regulation the composition of any of claims 1 to 4, or a salt thereof, in an amount effective for said negative regulation of Vpr function.

6. A method of treating HIV infection or AIDS, which comprises administering to a subject infected with HIV or with AIDS in need of such treatment an effective amount of a composition comprising the compound of any one of claims 1–4, or a salt thereof.

7. The method according to claim 6, wherein the subject is a mammal.

8. The method according to claim 7 wherein the mammal is human.

9. A method of treating HIV infection by suppressing maturation of HIV, which comprises administering to a subject infected with HIV in need of such suppression a therapeutically effective amount of the composition of any one of claim 1 to 4, or a salt thereof.

10. A method of treating HIV infection by reducing pathogenicity of HIV, which comprises administering to a subject infected with HIV in need of such reduction a therapeutically effective amount of the composition of any one of claim 1 to 4, or a salt thereof.

* * * * *

UNITED STATES PATENT AND TRADEMARK OFFICE
CERTIFICATE OF CORRECTION

| | |
|---|---|
| PATENT NO. | : 7,148,244 B2 |
| APPLICATION NO. | : 10/474600 |
| DATED | : December 12, 2006 |
| INVENTOR(S) | : Hideki Tanaka |

It is certified that error appears in the above-identified patent and that said Letters Patent is hereby corrected as shown below:

In claim 1 at column 19, line 35, please delete "A-B-D-E-" and insert therefor --A-B-D-E--.

Signed and Sealed this

Twenty-second Day of May, 2007

JON W. DUDAS
*Director of the United States Patent and Trademark Office*

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial sequence
<220> FEATURE:
<223> OTHER INFORMATION: A peptide tag for protein purification and
      detection

<400> SEQUENCE: 1

Asp Tyr Lys Asp Asp Asp Asp Lys
1               5

<210> SEQ ID NO 2
<211> LENGTH: 65
<212> TYPE: DNA
<213> ORGANISM: HIV

<400> SEQUENCE: 2
ctccctcgag ggcaccatgg actataagga cgacgacgac aacatggaac aagcccaga      60 agacc                                                                 65
```

```
<210> SEQ ID NO 3
<211> LENGTH: 32
<212> TYPE: DNA
<213> ORGANISM: HIV

<400> SEQUENCE: 3
ctttctagac taggatctac tggctccatt tc                                 32

<210> SEQ ID NO 4
<211> LENGTH: 29
<212> TYPE: DNA
<213> ORGANISM: HIV

<400> SEQUENCE: 4
tctccctcga gggcaccatg gactataag                                     29

<210> SEQ ID NO 5
<211> LENGTH: 35
<212> TYPE: DNA
<213> ORGANISM: HIV

<400> SEQUENCE: 5
cgacatctag actagaaatg gataaacagc agttg                              35
```